US005702393A

United States Patent [19]
Pfaifer

[11] Patent Number: 5,702,393
[45] Date of Patent: Dec. 30, 1997

[54] ASSEMBLY DEVICE FOR ELONGATE COMPONENTS OF OSTEOSYNTHESIS, ESPECIALLY SPINAL, EQUIPMENT

[75] Inventor: Patrick Pfaifer, Lyons, France

[73] Assignee: Groupe Lepine, Lyons, France

[21] Appl. No.: 758,669

[22] Filed: Dec. 2, 1996

[30] Foreign Application Priority Data

Dec. 7, 1995 [FR] France .................... 95 14735

[51] Int. Cl.$^6$ .................... A61B 17/56; A61F 2/44
[52] U.S. Cl. .................... 606/61; 606/73; 623/17
[58] Field of Search .................... 623/16, 17; 606/60, 606/61, 72, 73

[56] References Cited

U.S. PATENT DOCUMENTS

| | | | |
|---|---|---|---|
| 4,946,458 | 8/1990 | Harms et al. | 623/17 X |
| 5,217,497 | 6/1993 | Mehdian | 606/61 X |
| 5,360,431 | 11/1994 | Puno et al. | 623/17 X |
| 5,385,583 | 1/1995 | Cotrel | 606/61 X |
| 5,474,551 | 12/1995 | Finn et al. | 606/73 X |
| 5,474,555 | 12/1995 | Puno et al. | 623/17 X |
| 5,554,191 | 9/1996 | Lahille et al. | 623/17 |
| 5,591,235 | 1/1997 | Kuslich | 623/17 |

FOREIGN PATENT DOCUMENTS

| | | |
|---|---|---|
| A-0 509 322 | 4/1992 | European Pat. Off. . |
| A-0 578 320 | 7/1993 | European Pat. Off. . |

*Primary Examiner*—Mary Beth Jones
*Attorney, Agent, or Firm*—Oliff & Berridge, P.L.C.

[57] ABSTRACT

The assembly device of the present invention includes a body (10), a ring (11) and a nut (12);

the body includes:

a threaded upper portion (10a), two legs (15) delimiting between them a channel (16) for accommodating one (4) of the elongate components (4,5) to be assembled, these legs (15) being capable of moving apart or closer together;

at least one bearing surface (19) formed on the lateral face of the body (10) or of the legs (15), forming an axial stop, and a transverse aperture (20) in which the second elongate component (5) to be assembled may be engaged;

the ring (11) can be engaged over the body (10) until it comes to bear on the stop (19), and is dimensioned in such a way that in this position it lies around the legs (15);

the nut (12) can be screwed onto the threaded upper portion (10a) of the body (10).

8 Claims, 1 Drawing Sheet

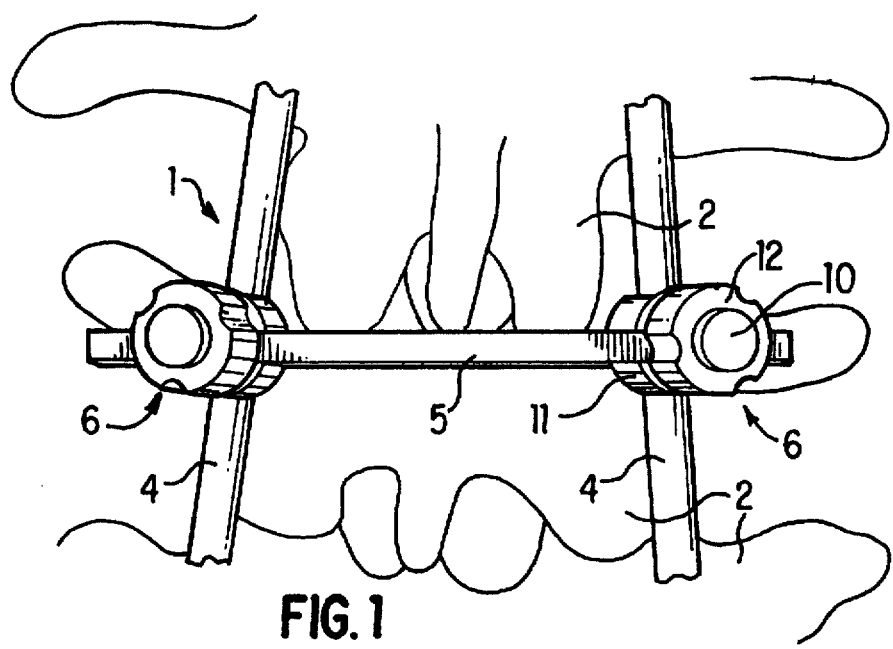
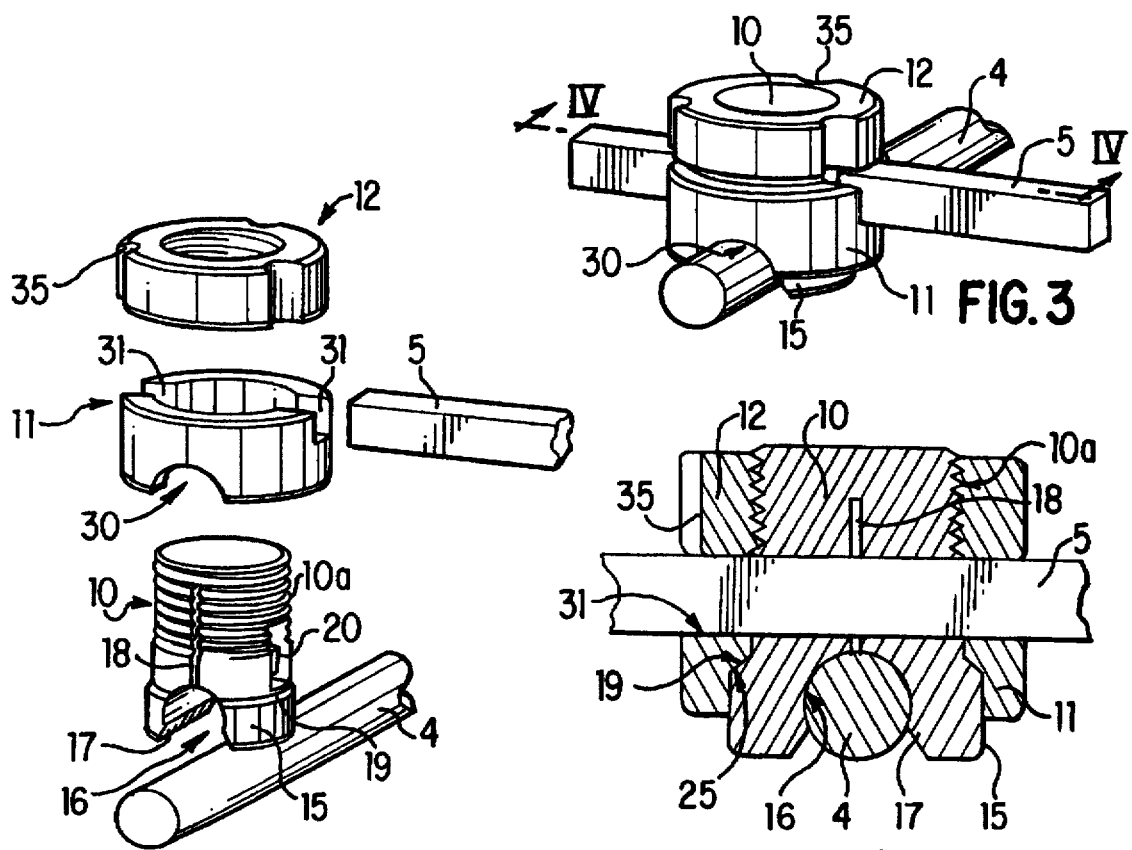

ASSEMBLY DEVICE FOR ELONGATE COMPONENTS OF OSTEOSYNTHESIS, ESPECIALLY SPINAL, EQUIPMENT

The present invention relates to an assembly device for elongate components of osteosynthesis, especially spinal, equipment. Two devices according to the invention are, in particular, intended to assemble two rods for supporting the spine and a crosspiece joining these rods together transversely.

Spinal osteosynthesis equipment generally comprises two support rods arranged parallel to one another on each side of the vertebrae, members for anchoring these rods to the vertebrae, such as hooks or pedicle screws, and crosspieces which join these rods together transversely by degrees in order to hold them relative to one another.

Assembling a crosspiece with two support rods by means of hook-shaped and fittings screwed onto the ends of the crosspiece, the curved parts of which hooks are engaged around the rods, is known.

The drawbacks of these devices are that they are relatively time-consuming and difficult to fit and give an assembly which in relative terms is not very rigid in terms of bending and of torsion.

Other devices designed to achieve such an assembly comprise a plurality of small components, especially clamping nuts or screws. Fitting and tightening these various components is time consuming and difficult to carry out.

Some devices have relatively limited surface areas for contact with the rods and/or the crosspiece, and in the long term this may lead to risks of slippage or of working slack under the effect of the repeated stresses to which the equipment is subjected as the patient moves.

SUMMARY OF THE INVENTION

The invention aims to overcome all of these drawbacks by providing a device which is easy and quick to fit, gives good rigidity in terms of torsion and of bending, and eliminates any risk of slippage or of working slack of the assembled components.

The device according to the invention comprises a body, a ring and a nut;

the body includes:

a threaded upper portion, two legs projecting from its lower end, and a channel being defined between the two legs. The channel is sized to accommodate an elongate component, with the elongate component comprising a rod that extends along the spine for support. The two legs being capable of moving apart or closer together so that when they are in a relatively spaced-apart position they allow the elongate component to be inserted into said channel, and when they are in a relatively close-together position they prevent the elongate component from being withdrawn from said channel;

at least one bearing surface formed on the lateral face of the body or of the legs, forming an axial stop, and a transverse aperture in which the second elongate component to be assembled may be engaged;

the ring can be engaged over the body until it comes to bear on the stop, and is dimensioned in such a way that in this position it lies around the legs and holds them in the aforementioned relatively close-together position;

the nut can be screwed onto the threaded upper portion of the body, the assembly being shaped in such a way that the nut, while being screwed on, clamps said second elongate component to be assembled and the ring against the aforementioned stop.

Tightening the nut thus makes it possible to hold the ring around the legs, and therefore hold the legs in their relatively close-together position, allowing the first elongate component to be assembled to be retained, and simultaneously makes it possible to clamp the second component to be assembled between itself and the ring, and therefore ensure that this second component is immobilized and assembled with the first component.

The advantage of this device is that it is easy and quick to fit, particularly on support rods after these have been fixed to the spine.

The three components forming this device have dimensions allowing easy manipulation. Furthermore, the aforementioned legs and the aforementioned aperture have substantial surface areas for contact with the elongate components to be assembled, and this eliminates any risk of slippage or working slack between these components.

Advantageously, the stop and the ring are shaped to allow the legs to move closer together as the nut is tightened, so as to clamp the legs into the elongate component to be assembled. This clamping makes it possible to immobilize this comopnent with respect to the legs, so that the stresses exerted on the equipment as the patient moves can be withstood.

According to a preferred embodiment of the invention in this case, the stop consists of a conical shoulder and the ring comprises a complementary conical shoulder. The movement of these shoulders with respect to one another as the nut is tightened makes it possible to move the legs toward each other.

Preferably, the ring is shaped in such a way as to come to bear on said first component to be assembled as the nut is tightened. It thus makes it possible to increase the surface areas the device has for contact with this component.

According to a preferred embodiment of the invention in this case, the ring comprises two notches formed in its lower edge, diametrically opposite one another.

Advantageously, the ring comprises two notches formed in its upper edge, these being intended to come to face the aperture of the body accommodating said second elongate component to be assembled. These notches favor guidance of this second component to be assembled, in order to engage it in the aperture.

These various notches make it possible to reduce the height of the assembly device. The notches formed in the lower edge of the ring allow the other two notches to be positioned instantly facing the aperture of the body. Furthermore and above all, these notches make it possible to secure the ring with respect to the two elongate components to be assembled so that the ring constitutes an additional means of holding these components and of spreading the bending or torsion loads which the device may be called upon to withstand.

Advantageously, the legs comprise, on their faces opposite each other and in the region of their free ends, projecting beadings situated a distance apart which is less than the width of the elongate component to be assembled which is intended to be accommodated in the channel.

These beadings allow this component to be snap-fitted between the legs, so that the body of the device can be held temporarily on the component to be assembled for the time required for the ring and nut to be fitted.

As a preference, the body comprises a longitudinal middle slot emerging in the bottom of the channel delimited by the legs, this slot being capable of increasing the possibility for movement of the legs relative to one another, especially in order to facilitate their clamping or snap-fitting.

BRIEF DESCRIPTION OF THE DRAWINGS

To make it easy to understand, the invention is described again hereinbelow with reference to the appended diagrammatic drawing which represents, by way of nonlimiting example, one preferred embodiment of the device to which it relates.

FIG. 1 is a perspective view of two of the devices of the invention for assembling elongate components which spinal osteosynthesis equipment comprises;

FIG. 2 is an exploded perspective view of the various elements of the invention, and of two components which are to be assembled using this device;

FIG. 3 is a perspective view of the device of the invention and of two elongate components, after assembly, and FIG. 4 is a cross sectional view of the invention taken along the line IV—IV of FIG. 3.

DESCRIPTION OF THE PREFERRED EMBODIMENT

FIG. 1 represents a portion of spinal osteosynthesis equipment 1, implanted on the vertebrae 2 of a spine.

The equipment 1 comprises two support rods 4 arranged parallel to one another on each side of the vertebrae 2, members for anchoring these rods 4 to the vertebrae 2, such as hooks or pedicle screws (not represented because they are well known in themselves), at least one crosspiece 5 which joins these rods 4 together transversely, in order to hold them relative to one another, and at least two devices 6 assembling the rods 4 and the crosspiece 5.

As is clear from FIGS. 2 to 4, the device 6 comprises a body 10 of cylindrical overall shape, a ring 11 and a nut 12.

The body 10 includes:

a threaded upper portion 10a;

two legs 15 projecting from its lower end, delimiting between them an approximately semi-circular channel 16 for accommodating one of these rods 4; these legs 15 comprise, on their faces opposite each other and in the region of their free ends, projecting beadings 17 situated a distance apart which is less than the diameter of the rods 4;

a longitudinal middle slot 18 emerging in the bottom of the channel 16;

a conical shoulder 19 formed on the outer lateral face of the legs 15, forming an axial stop, and a transverse aperture 20 through which the crosspiece 5 may be engaged; this aperture 20 has a height which is greater than that of the crosspiece 5 and extends in part along the threaded portion 10a.

The ring 11 has an inside diameter which, to within a clearance, corresponds to the diameter of the body 10, and also comprises a conical shoulder 25 at its lower part capable of coming into abutment against the shoulder 19 when the ring 11 is engaged over the body 10.

The ring 11 is extended downwards beyond the shoulder 25, as shown in FIG. 4, so that it lies around the legs 15 when the shoulder 25 comes to bear against the shoulder 19.

Furthermore, the ring 11 comprises two semi-circular notches 30 formed in its lower edge, diametrically opposite one another, and two notches 31 of square shape formed in its upper edge, these also being arranged so that they are diametrically opposite one another. The notches 31 are arranged at right angles to the notches 30.

The nut 12 can be screwed onto the threaded portion 10a. To rotate it, it comprises three grooves 35 formed in its peripheral wall, which are intended to take the corresponding pins of a box wrench (not represented).

In practice, the pedicle hooks or screws are fitted into the vertebrae 2 and the rods 4 are fixed to them.

To assemble a crosspiece 5 to the rods 4, the bodies 10 of two devices 6 are snap-fitted onto each of the rods 4, facing one another. This snap-fitting is made possible by slot 18 which gives the legs 15 a certain degree of mobility allowing them to move apart as change beadings 17 fit over a rod 4 and the rod 4 is introduced into the channel 16 hold rods 4 in channels 16, and the return elastically the legs 15 after beadings 17 have cleared the outer diameter of rods 4 to their original position.

Each ring 11 is then introduced over the corresponding body 10 until its shoulder 25 comes to bear against the shoulder 19. In this bearing position, the notches 30 are engaged around the rod 4, and the notches 31 are placed facing the lateral openings of the aperture 20.

The crosspiece 5 is then engaged through the aperture 20. The notches 31 make this introduction easier.

Finally, the nut 12 is screwed onto the threaded portion 10a.

This nut 12, while being screwed on, clamps the crosspiece 5 and the ring 11 against the shoulder 19.

This clamping causes slight slippage of the shoulder 25 with respect to the shoulder 19, which causes the legs 15 to move closer together, making it possible to clamp these legs 15 onto the rod 4. At the same time the nut 12 clamps the crosspiece 5 between itself and the ring 11, and makes it possible to immobilize this crosspiece 5 and therefore assemble it with the rod 4.

The invention provides an improved device for assembling elongate components of osteosynthesis, especially spinal, equipment, having the numerous advantages indicated earlier, especially those of being easy and quick to fit, of displaying good rigidity in torsion and in bending, and of eliminating any risk of slippage or of working slack between the assembled components.

What I claim is:

1. An assembly device for connecting elongate components, said assembly device comprising:

a body, said body having a threaded upper portion and two legs extending from said threaded upper portion with said two legs delimiting between them a channel for accommodating a first one of said elongate components, said legs being capable of deflection relative to one another with such deflection changing the dimensions of said channel from a securing position of said legs for securing said first one of said elongate components within said channel to a releasing position of said legs for releasing said first one of said elongate components from said channel, a portion of an outer periphery of said body defining a bearing surface, a transverse portion of said body defining a transverse aperture through said body with said transverse aperture being dimensioned for allowing passage of a second one of said elongate components;

a ring fitting around said body and resting against said bearing surface when said legs are deflected to said securing position; and a nut being threadedly engaged with said threaded upper portion and exerting an axial force against said ring for retaining said second one of said elongate components within said transverse aperture and pressing said ring against said bearing surface.

2. The device according to claim 1, wherein a surface of said ring resting against said bearing surface is tapered such that said axial force exerted by said nut creates a transverse force on said legs deflecting said legs to said securing position.

3. The device according to claim 2, wherein said surface of said ring and said bearing surface comprise mating conical shoulders.

4. The device according to claim 1, wherein a portion of said ring defines a contoured support surface for bearing on an outer periphery of said first one of said elongate components when said ring rests against said bearing surface of said body.

5. The device according to claim 4, wherein said ring includes two diametrically opposed contoured support surfaces extending upwardly from a bottom surface of said ring.

6. The device according to claim 1, wherein said ring includes two diametrically opposed notches extending downwardly from an upper surface of said ring, with said notches being adjacent opposite ends of said transverse aperture.

7. The device according to claim 1, wherein said legs include opposed projecting beadings depending from free ends of said legs and extending into said channel.

8. The device according to claim 1, wherein a central axial portion of said body defines a longitudinal slot extending from a bottom of said channel between said legs a sufficient distance along said body to enhance the ability of said legs to flex relative to each other.

* * * * *

UNITED STATES PATENT AND TRADEMARK OFFICE
CERTIFICATE OF CORRECTION

PATENT NO. : 5,702,393

DATED : December 30, 1997

INVENTOR(S) : Patrick PFAIFER

It is certified that error appears in the above-indentified patent and that said Letters Patent is hereby corrected as shown below:

On the cover page,

In Item [75], please change "Lyons" to --Lyon--; and

In Item [73], please change "Lyons" to --Lyon--.

Signed and Sealed this

Twenty-fourth Day of February, 1998

Attest:

BRUCE LEHMAN

Attesting Officer  Commissioner of Patents and Trademarks